ð US009642970B2

(12) United States Patent
Shaw et al.

(10) Patent No.: US 9,642,970 B2
(45) Date of Patent: May 9, 2017

(54) SYRINGE WITH RETRACTABLE NEEDLE AND MOVEABLE PLUNGER SEAL

(75) Inventors: Thomas J. Shaw, Frisco, TX (US); Ni Zhu, Plano, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 298 days.

(21) Appl. No.: 12/827,548

(22) Filed: Jun. 30, 2010

(65) Prior Publication Data

US 2012/0004621 A1 Jan. 5, 2012

(51) Int. Cl.
*A61M 5/32* (2006.01)
*A61M 5/50* (2006.01)

(52) U.S. Cl.
CPC ........... *A61M 5/3234* (2013.01); *A61M 5/508* (2013.01); *A61M 2005/3239* (2013.01)

(58) Field of Classification Search
CPC .............. A61M 5/315; A61M 5/31513; A61M 5/31515; A61M 5/322; A61M 5/3221; A61M 5/3232; A61M 5/3234; A61M 5/50; A61M 5/5013; A61M 5/508; A61M 2005/323; A61M 2005/3231; A61M 2005/3235; A61M 2005/3236; A61M 2005/3239; A61M 2005/3241
USPC ....... 604/110, 187, 200, 201, 205, 218, 220, 604/221, 222, 231
See application file for complete search history.

(56) References Cited

U.S. PATENT DOCUMENTS

| 5,053,010 | A | * | 10/1991 | McGary .............. A61M 5/3234 604/110 |
| 5,064,419 | A | | 11/1991 | Gaarde |
| 5,180,369 | A | | 1/1993 | Dysarz |
| 5,180,370 | A | | 1/1993 | Gillespie |
| 5,201,710 | A | | 4/1993 | Caselli |
| 5,578,011 | A | | 11/1996 | Shaw |
| 5,935,104 | A | | 8/1999 | Janek et al. |
| 6,015,438 | A | * | 1/2000 | Shaw ............................ 604/195 |
| 6,099,500 | A | | 8/2000 | Dysarz |
| 6,228,054 | B1 | | 5/2001 | Dysarz |
| 6,994,690 | B2 | | 2/2006 | Kiehne |
| 7,544,182 | B2 | | 6/2009 | Kiehne |
| 2006/0111671 | A1 | | 5/2006 | Klippenstein |
| 2007/0060893 | A1 | * | 3/2007 | Mahurkar ...................... 604/187 |
| 2008/0287881 | A1 | * | 11/2008 | Kiehne ........................ 604/195 |
| 2010/0004597 | A1 | | 1/2010 | Gyrn et al. |

(Continued)

FOREIGN PATENT DOCUMENTS

RU 2452520 6/2012

*Primary Examiner* — Edelmira Bosques
*Assistant Examiner* — Larry R Wilson
(74) *Attorney, Agent, or Firm* — Ross Barnes LLP; Monty L. Ross; Robin L. Barnes

(57) ABSTRACT

A medical device having a barrel, a retractable needle, a needle retraction assembly and a plunger, the needle retraction assembly including and being held inside the barrel prior to retraction at least in part by a retainer member contacting the barrel, the plunger comprising a plunger seal with an body having at least a portion that is rearwardly moveable relative to the plunger and an elastomeric web that seals a retraction cavity inside the plunger prior to retraction of the needle, the retainer member and the plunger seal each cooperating with an inside wall of the barrel to provide a sealed liquid containment chamber inside the device.

14 Claims, 11 Drawing Sheets

(56) References Cited

U.S. PATENT DOCUMENTS

2010/0010450 A1    1/2010  Runfola et al.
2011/0178507 A1*  7/2011  Bracken et al. .............. 604/544

* cited by examiner

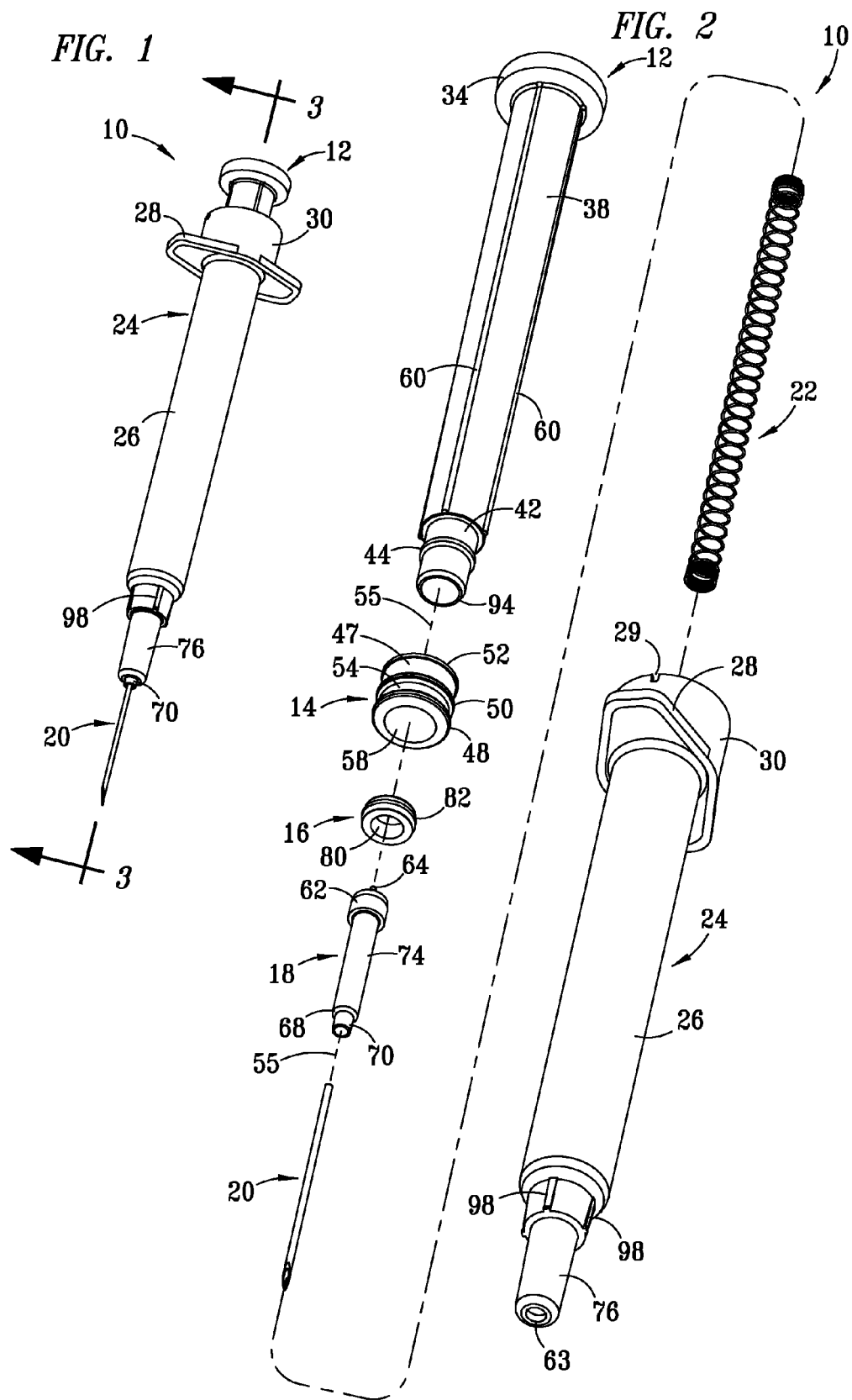

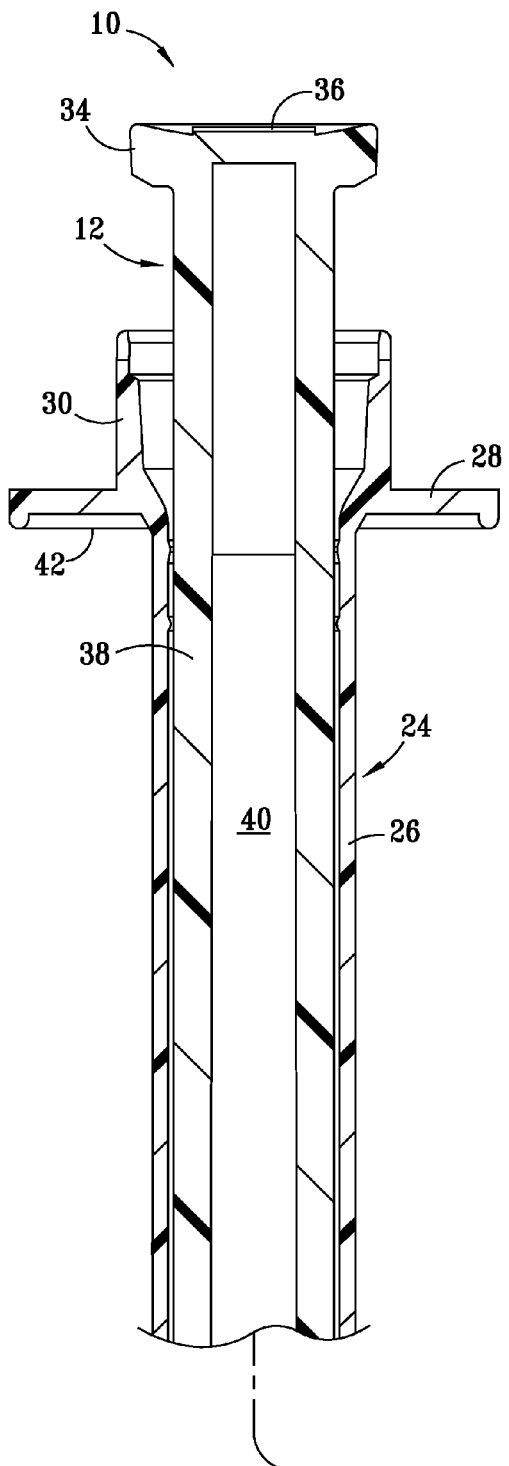
FIG. 3
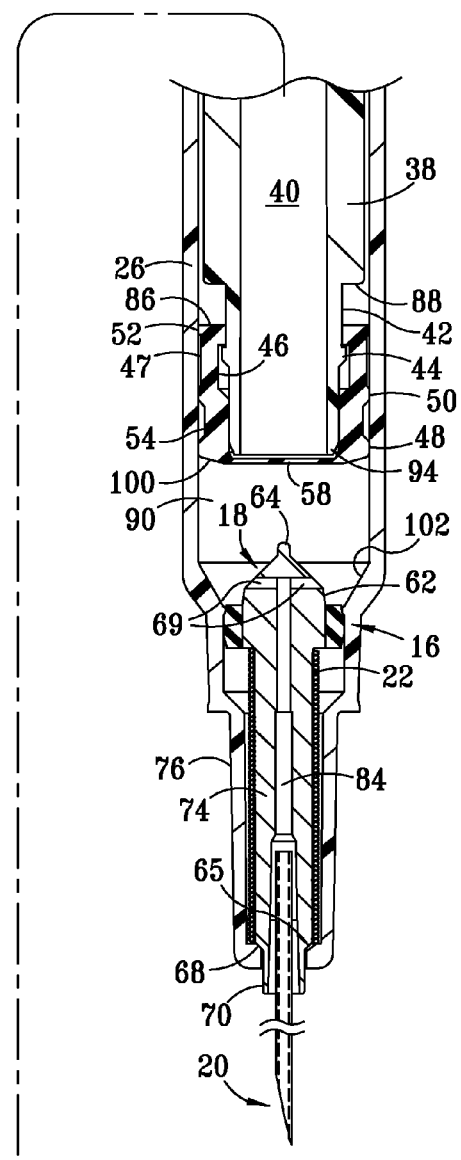
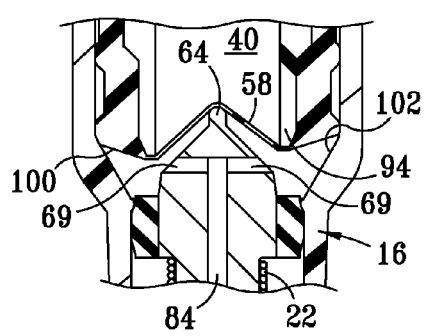
FIG. 4

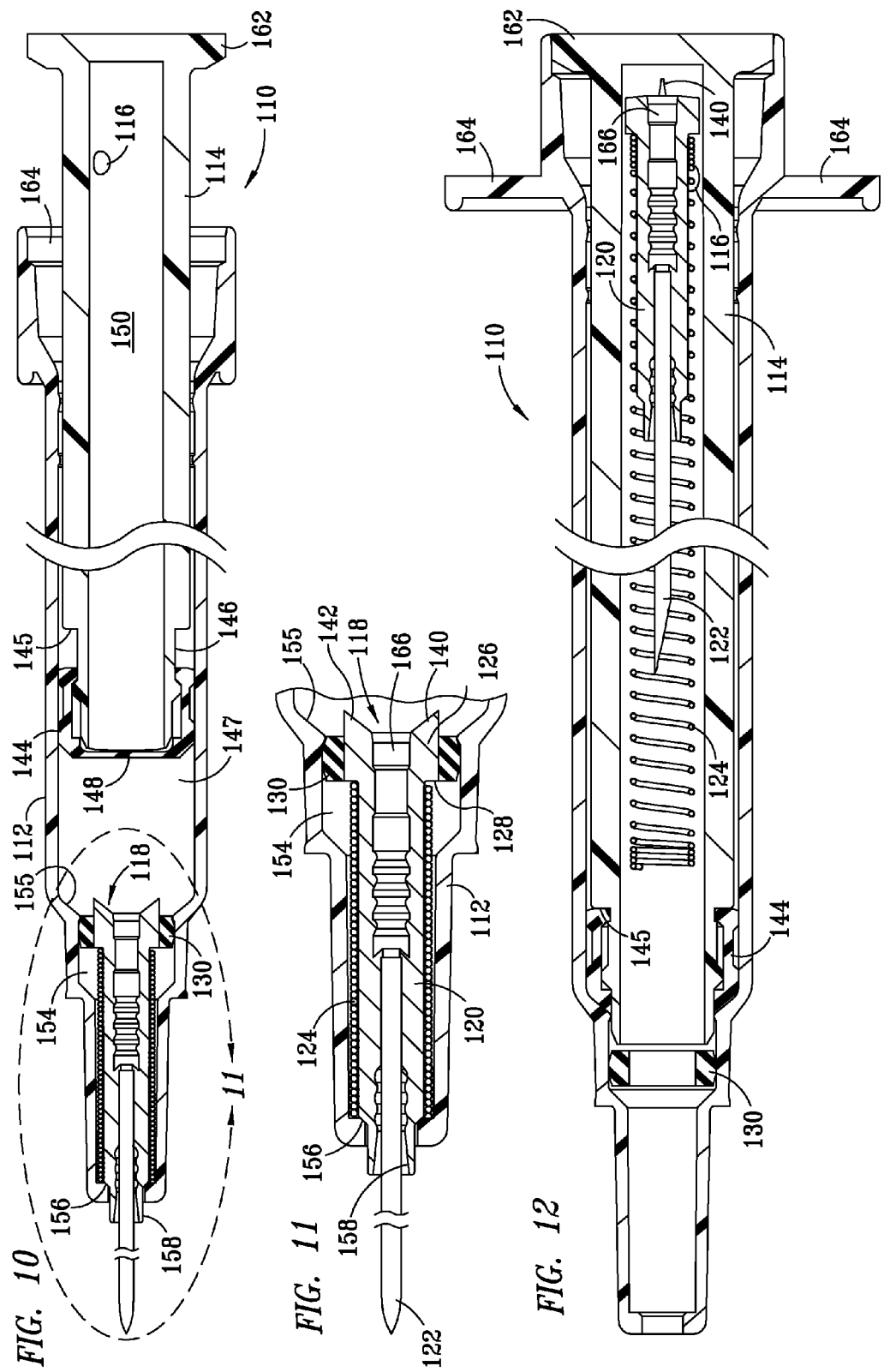

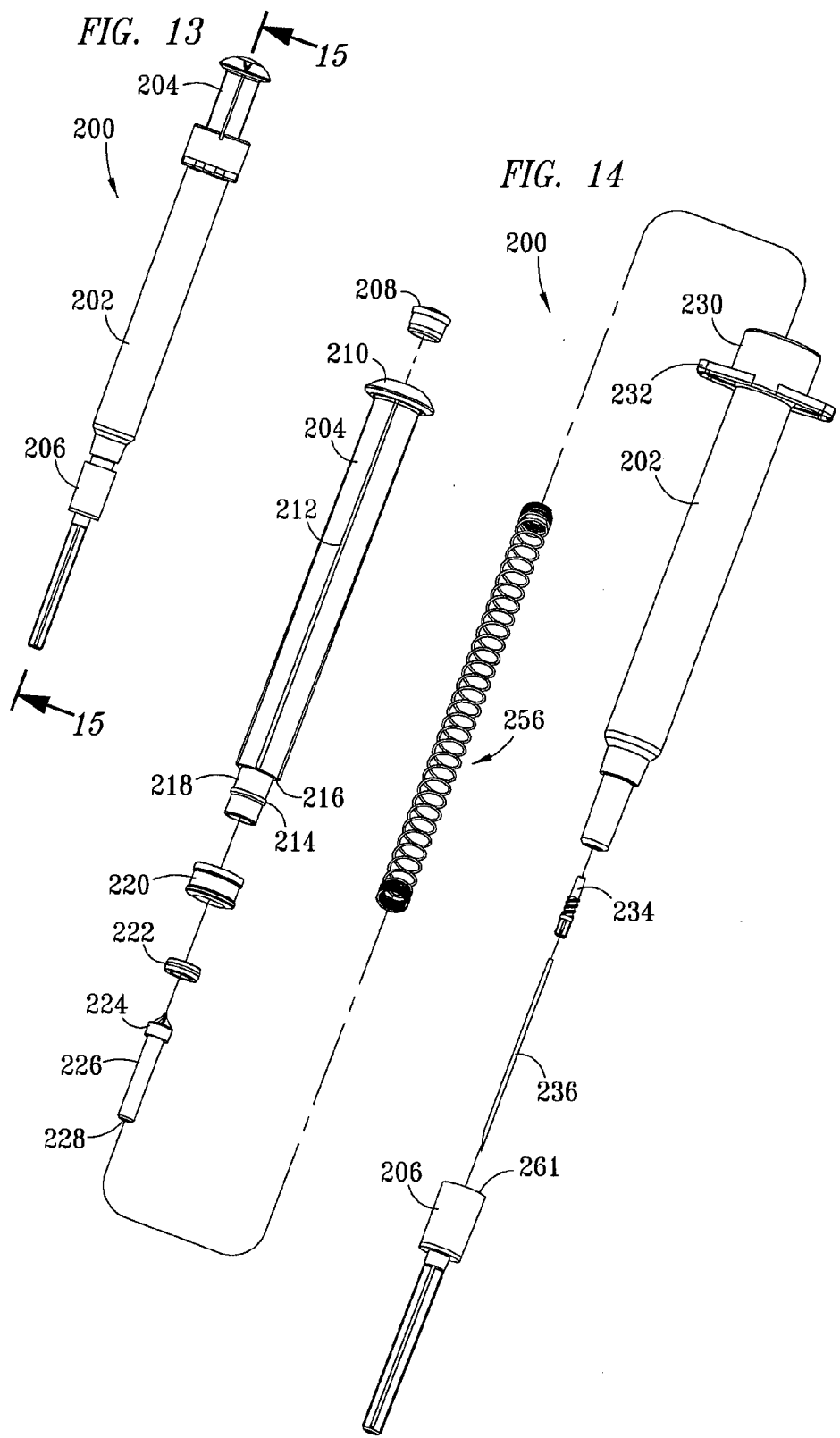

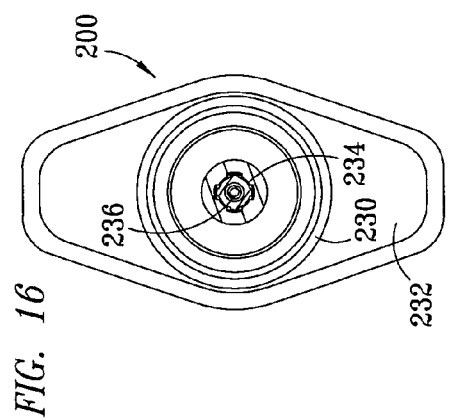
FIG. 16
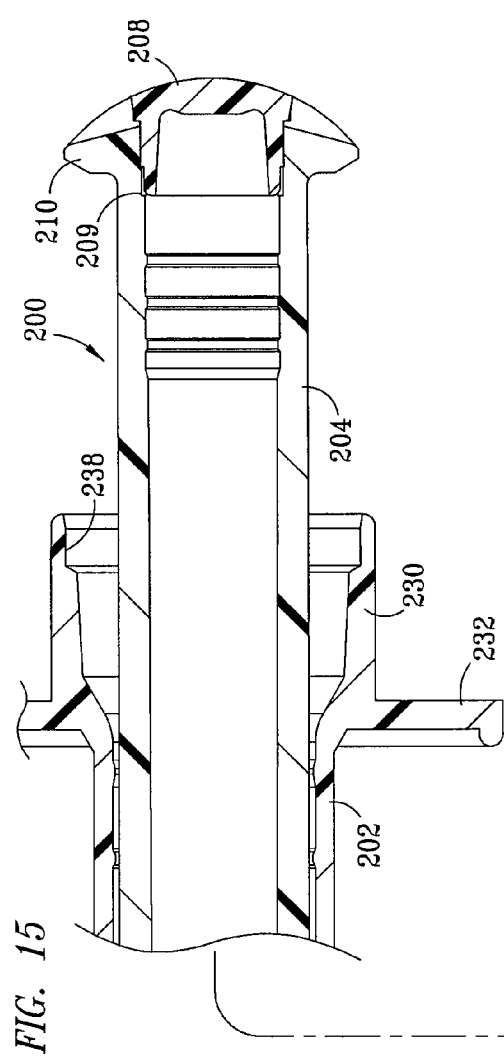
FIG. 15
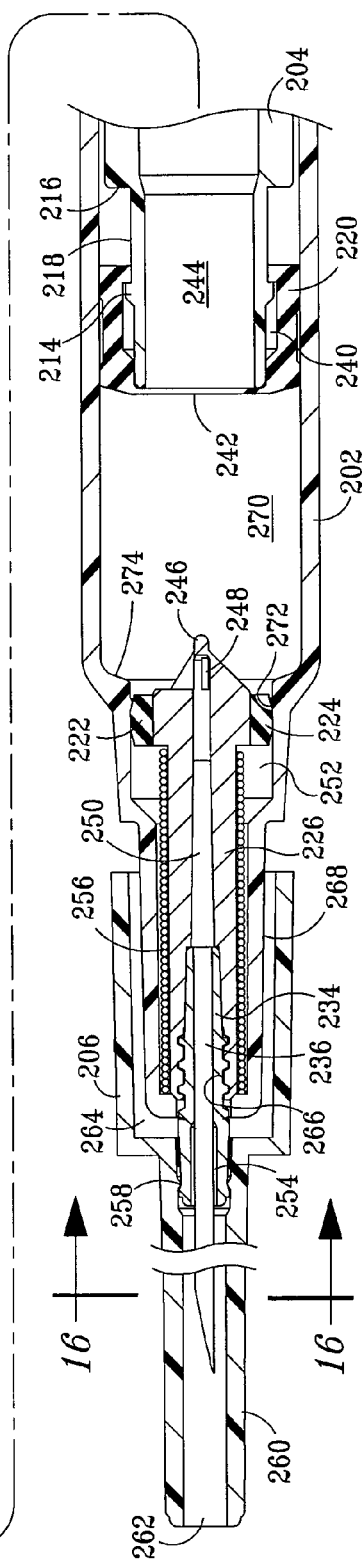

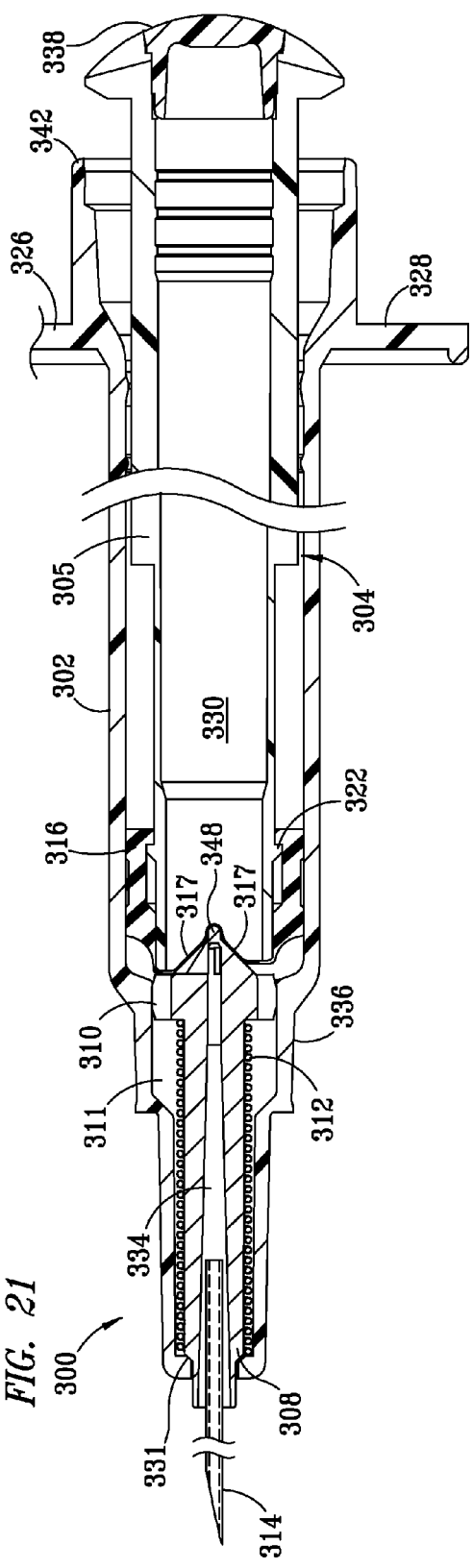

SYRINGE WITH RETRACTABLE NEEDLE AND MOVEABLE PLUNGER SEAL

TECHNICAL FIELD

This invention relates to medical devices having needles that are retractable following use to reduce the likelihood of reuse, needle-stick injuries and accidental contamination of healthcare workers and patients, especially by the transmission of pathogens carried by bodily fluids. More particularly, the invention relates to a medical device having an elastomeric retainer ring and an elastomeric plunger seal moveable on the plunger that cooperate to provide smoother operation and to significantly reduce the pressure that must be applied by a user to retract the needle.

BACKGROUND ART

In the past, clinicians have sometimes complained about the magnitude of the thumb force (sometimes called the "retraction force," "activation force" or "total force") that is required to initiate needle retraction in syringes having retractable needles. When using conventional syringes having needles that are retracted by the expansion of a compressed spring, an additional thumb force is typically applied axially at the back of the plunger handle following injection to initiate needle retraction. The magnitude of the thumb force that is required depends upon the structure and operation of each particular syringe. One part of the required thumb force is attributable to the force needed to break, rupture, remove or displace the cover over the opening into a retraction cavity inside the plunger handle. Another part of the required thumb force is attributable to the force needed to release whatever structure is holding the spring in compression. If the required thumb force is too great, especially for clinicians having small hands, it can be difficult to retract the needle after an injection. This can cause the user to move or twist the syringe while a needle is still inside the patient in order to gain more leverage. Also, unless the structural elements of the device are configured so that the thumb force can be applied smoothly so as to open the retraction cavity and release the compressed spring without jerks or abrupt movement prior to retraction.

Some prior art syringes have utilized a plug or substantially rigid barrier to block the entrance to a retraction cavity inside the plunger handle prior to retraction, but the force required to dislodge or displace the plug, or to fracture the substantially rigid barrier, also increased the required thumb force. Other prior art syringes have used an axially fixed plunger seal having a rubbery portion covering the opening to the retraction cavity in combination with a two-part plunger handle in which an inner member had to be moved past a detent to advance a cutter that severed the covering portion, thereby also increasing the required thumb force. In such cases, the force required to dislodge a plug, fracture a barrier or move a plunger section past a detent not only increased the thumb force required to initiate retraction but also caused the syringe to jerk or move abruptly prior to needle retraction.

U.S. Pat. No. 5,053,010 (McGary) discloses a syringe having a retractable needle and a plunger with an axially slidable plunger seal having a transverse web portion that seals the opening into the plunger retraction cavity prior to retraction. That syringe has a cutting tool disposed on the forwardly extending tip of the plunger that cuts through both the transverse web across the opening to the retraction cavity and another circumferentially extending tab that secures the needle retainer to the barrel wall. Because of the cutter positioned behind the transverse web, there is a risk of premature rupture of the web during injection, which is not desirable because the remaining portion of medicine in the syringe could flow back into the retraction cavity rather than into the patient.

U.S. Pat. No. 5,064,419 (Gaarde) discloses a syringe having a retractable needle and a piston with a piston packing that is confined to prevent axial movement relative to the piston. FIG. 3 discloses a thin membrane attached to the piston packing. The thin membrane seals off a cavity inside the piston until the flat head of the needle holder punctures or destroys the membrane for retraction. The needle holder is held in place by the closed bottom end of a barrel section that is disposed inside the spring retainer.

U.S. Pat. No. 5,180,369 (Dysarz) discloses a syringe having a retractable needle and a gasket disposed between the plunger and the barrel that is axially slidable on the plunger. That syringe has a shatter plate that seals the opening into the retraction cavity inside the plunger prior to retraction. The needle holder is held in place prior to retraction by a shatter plate and shatter ring, each of which requires an additional gasket to provide a fluid seal.

U.S. Pat. No. 5,180,370 (Gillespie) discloses a syringe having a retractable needle and an annular seal ring that provides a fluid seal between the plunger and barrel. The annular seal ring does not appear to be confined to prevent axial movement relative to the plunger but does not appear to slide axially relative to the plunger during use. The plunger has a hollow chamber that is sealed from the interior of the barrel by a resilient rupturable cover.

U.S. Pat. No. 5,201,710 (Caselli) discloses a syringe having a retractable needle held by a needle holder having a head with a sharp part shaped like a crown with a sharp edge that first bends and then breaks a diaphragm connected to a plunger seal element that is confined to prevent axial sliding relative to the plunger cylinder.

U.S. Pat. No. 5,578,011 (Shaw) discloses a syringe having a retractable needle and an elastomeric friction ring to hold the needle holder inside the barrel and to provide a fluid seal between the barrel wall and the needle holder. That syringe has a plunger seal that is confined from sliding axially along the plunger, and an elastomeric plug that provides a releasable seal inside the front opening to the retraction cavity inside the plunger.

U.S. Pat. No. 6,015,438 (Shaw) discloses a syringe having a retractable needle, an annular retainer member to hold the needle holder inside the barrel and an a plunger seal disposed between the plunger and the barrel that is axially slidable along the plunger for retraction. That syringe has a separate, removable stopper that seals the opening into the retraction cavity inside the plunger prior to retraction.

U.S. Pat. No. 6,994,690 (Kiehne) and U.S. Pat. No. 7,544,182 (Kiehne) disclose syringes having a retractable needle and a tapered extension on the inner part of the head of the needle holder that projects rearwardly to burst or pierce a frangible portion of a fixed plunger seal as the plunger is advanced against the needle holder. However, in those syringes the plunger seal is axially confined and cannot slide rearwardly in relation to the front of the plunger to stretch the frangible portion tautly from the barrel side as the plunger contacts the needle holder.

A medical device having a retractable needle is therefore needed that can be operated smoothly to initiate needle retraction and that reduces the thumb force required to initiate retraction

SUMMARY OF THE INVENTION

The medical devices of the invention desirably comprise a barrel, a plunger slidably engaging the barrel, and a needle retraction assembly that can be selectively activated to retract the needle by moving the plunger forward relative to the barrel. The needle retraction assembly can desirably comprise an elastomeric retainer ring that contacts an inside wall of the barrel to help create a liquid seal between a needle holder and the inside wall of the barrel, and that helps hold a needle retraction spring in compression prior to needle retraction. The plunger desirably comprises an elastomeric seal with an annular body portion and a transverse elastomeric web portion. The annular body can function as a liquid seal between the plunger and barrel, and the transverse web portion can seal off an opening into a retraction cavity disposed inside the plunger prior to retraction.

The annular body portion of the plunger seal can be mounted on the front portion of the plunger in such manner that the body portion is axially moveable relative to the outside wall of the plunger to stretch and thin the transverse web across the opening into the retraction cavity without prematurely rupturing the transverse web portion prior to initiating needle retraction. The forwardly facing annular end of the plunger, disposed behind the transverse elastomeric web, is preferably configured so as not to cut the elastomeric web when the web is stretched across the opening into the retraction cavity prior to retraction, but can be configured to exert a force that is either evenly or unevenly distributed around the circumference of the retainer ring as desired. An unevenly distributed force can reduce the force required to initiate movement of the retainer ring relative to the barrel prior to retraction. The force of the plunger is typically applied to the retainer ring through that portion of the plunger seal that covers the front tip end of the plunger handle, although, a portion of the plunger handle can contact the retainer ring directly in some cases such as, for example, if the elastomeric web ruptures prior to contacting the retainer ring.

Prior to retraction, the needle and needle holder portions of the needle retraction assembly can be biased rearwardly by a compressed spring. The biasing force is desirably slightly less than a holding force exerted on the needle holder portion by a retainer member that establishes a liquid seal between the inside of the barrel and the needle holder, and that maintains the front tip of the needle holder in a forwardly projecting position relative to the barrel until retraction. As the plunger is fully depressed inside the barrel, the body portion of the elastomeric plunger seal can be pushed rearwardly relative to the plunger and the transverse web portion of the elastomeric plunger seal can be stretched, thinned, and eventually penetrated, pierced or ruptured by a rearwardly projecting portion of the needle holder as the retainer member is displaced by the plunger to release the holding force exerted on the needle holder by the retainer member and the inside wall of the barrel. This in turn can allow the biasing force of the compressed spring to propel the needle holder, spring and needle rearwardly through the ruptured web of the elastomeric plunger seal and into the retraction cavity. As the plunger is fully depressed into the barrel, a thumb cap at the rear of the plunger can be lodged inside a cylindrical collar at the rear of the barrel so as to render the thumb cap substantially ungraspable for reuse.

The use of an elastomeric retainer ring in combination with a plunger seal having a body portion that is axially moveable rearwardly along the plunger and an elastomeric web portion that can be stretched and thinned by such rearward axial movement of the body portion prior to retraction is believed to provide smoother retraction and to substantially reduce the thumb force that must be applied by a user to initiate needle retraction. Smoother operation and a lower required thumb force are in turn believed to reduce motion of the needle tip either forwardly or laterally inside a patient prior to retraction, to promote the usage of devices having retractable needles by clinicians, and to thereby reduce the incidence of unwanted needle stick injuries and the associated spread of blood-borne pathogens due to inadvertent contamination by contact.

BRIEF DESCRIPTION OF THE DRAWINGS

The apparatus of the invention is further described and explained in relation to the following drawings wherein:

FIG. 1 is a perspective view of one embodiment of the medical device of the invention;

FIG. 2 is an exploded perspective view of the medical device of FIG. 1;

FIG. 3 is an enlarged, cross-sectional vertical elevation view taken along line 3-3 of FIG. 1 wherein the needle is in a forwardly projecting use position;

FIG. 4 is an enlarged detail view taken from FIG. 3 but showing the elastomeric seal across the front of the retraction cavity being distended by the rearwardly projecting head of the needle holder as the plunger tip moves forwardly inside the barrel;

FIG. 10 is an enlarged cross-sectional horizontal view, partially broken away, of another embodiment of the medical device of the invention wherein the needle is in a forwardly projecting use position;

FIG. 11 is an enlarged detail view taken as indicated in FIG. 10;

FIG. 12 is an enlarged cross-sectional horizontal view of the medical device of FIG. 10 but rotated 90 degrees around the longitudinal axis of the device, wherein the plunger is fully depressed into the barrel and wherein the needle is fully retracted;

FIG. 13 is an inclined elevation view of another embodiment of the medical device of the invention;

FIG. 14 is an exploded perspective view of the medical device of FIG. 13;

FIG. 15 is an enlarged, cross-sectional horizontal elevation view taken along line 3-3 of FIG. 1 wherein the needle is in a forwardly projecting use position and is covered by a protective cap;

FIG. 16 is a cross-sectional left side elevation view taken along line 16-16 of FIG. 15;

FIG. 21 is a cross-sectional elevation view of the embodiment of FIG. 21 wherein the rearwardly projecting head of the needle holder has engaged and stretched or distended the elastomeric web of the plunger seal rearwardly, and wherein the most forwardly extending portion of the plunger handle, covered by the elastomeric web of the plunger seal, is contacting the retainer member prior to needle retraction;

FIG. 22 is a cross-sectional elevation view of the embodiment of FIG. 21 following needle retraction.

DESCRIPTION OF THE PREFERRED EMBODIMENTS

Figure 5:
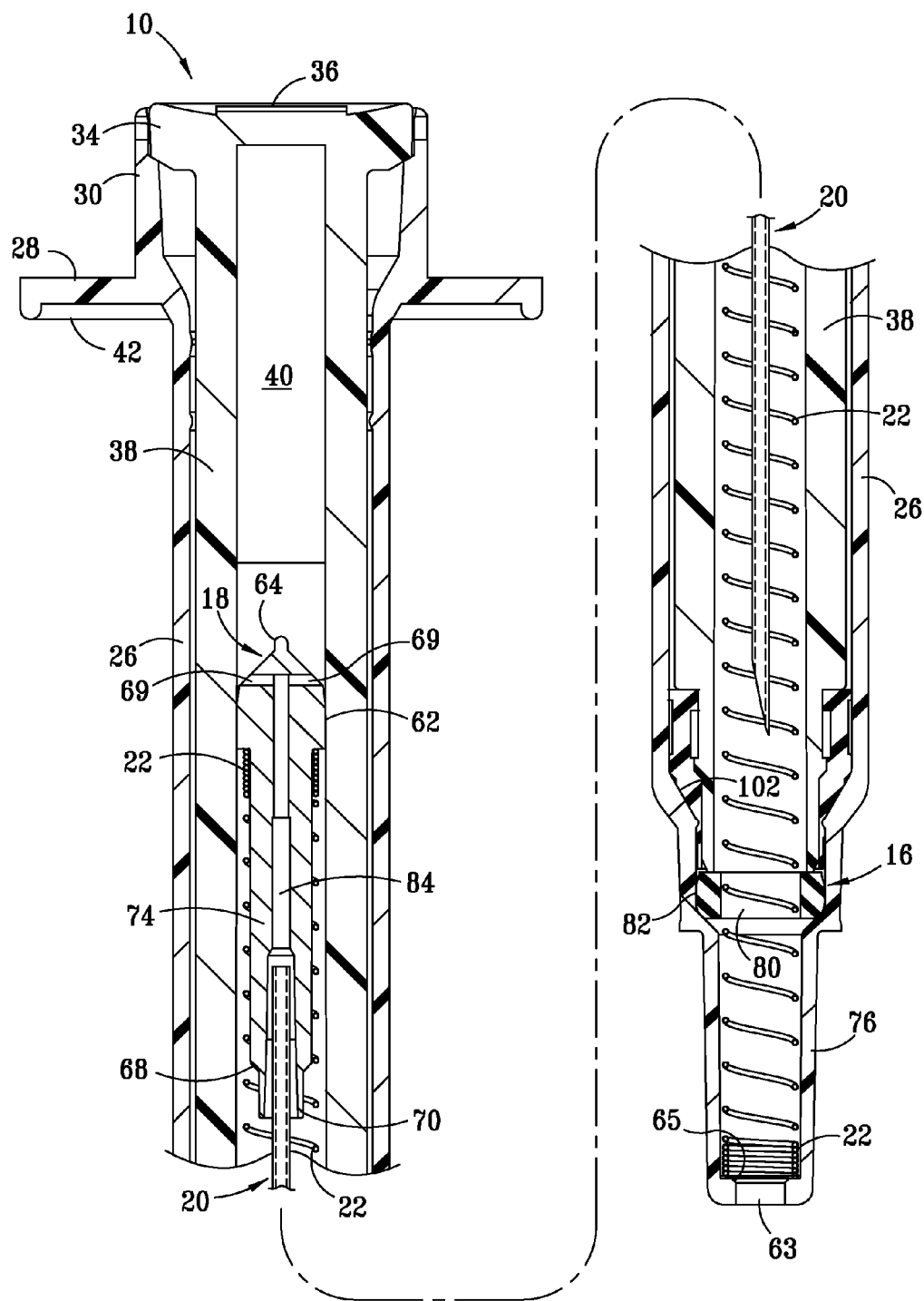
FIG. 5 is a cross-sectional elevation view of the medical device of FIG. 3 wherein the needle is in its fully retracted position.

One embodiment of the medical device of the invention is described and explained in relation to FIGS. 1-9, wherein syringe 10 comprises as its principal parts barrel 24, a needle retraction assembly installed in the front portion of barrel 24, and plunger assembly 12 that slidably engages an opening in the rear of the barrel. The needle retraction assembly comprises needle holder 18, needle 20, compression spring 22 and retainer member 16. A removable needle cover that protects the tip of needle 20 during packaging, shipment and storage is not shown in FIGS. 1-9, but a suitable needle cover is shown, for example, in relation to another embodiment of the invention as molded plastic needle cover 206 in FIGS. 13-14.

Barrel 24 comprises tubular body 26 with opposed radially extending flanges 28 providing contact surfaces for the index and middle fingers of a user, a larger diameter collar 30 disposed behind flanges 28, a smaller diameter front collar optionally comprising a plurality of arcuately spaced, longitudinally directed ribs 98 that provide a seating surface for a removable needle cover, and a tapered, forwardly extending nose 76 having an open end through which forward tip 70 of needle holder 18 desirably projects when the needle retraction assembly is seated inside barrel 24. Referring to FIG. 2, collar 30 is optionally provided with one or more notches 29 so that collar 30 can expand slightly if needed in order for collar 30 to receive end cap 34 of plunger assembly 12. The provision of notches 29 allows the use of closer tolerances between the inside diameter of collar 30 and the outside diameter of end cap 34 to insure a close fit between the two parts and make plunger end cap 34 less graspable following injection and retraction to help prevent reuse of syringe 10.

Plunger assembly 12 includes tubular body 38 with a larger diameter end cap 34, a plurality of optional, arcuately spaced, longitudinally extending ribs 60 disposed around body 38, annular surface 42, annular positioning ring 44, front tip 94, and elastomeric plunger seal 14. Plunger seal 14 is preferably unitarily molded from a compressible, rubbery material and comprises an annular body portion and a transverse web portion. The annular body portion of plunger seal 14 desirably comprises outwardly facing, axially spaced annular ridges 48, 50, 52 separated by annular recesses 54, 47, respectively, and an inwardly facing annular recess 46. It will be appreciated by those of skill in the art upon reading this disclosure that the forwardly disposed annular ridge or flange, as exemplified for example by annular ridge 48 in FIG. 6, performs the primary sealing function, while the second, spaced-apart annular flange such as ridge 50 in FIG. 6 primarily serves to align the plunger seal inside the barrel.

Figure 6:
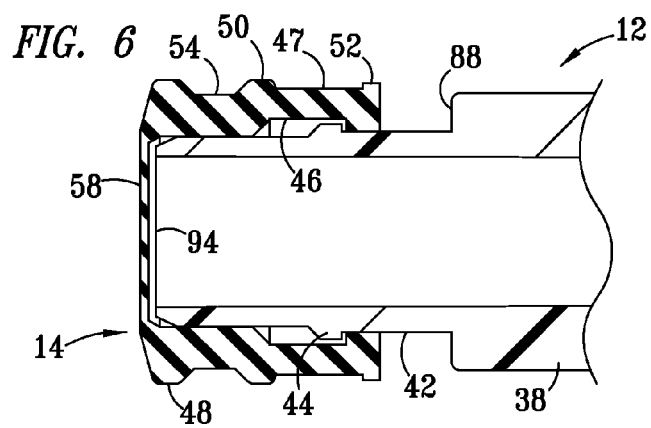
FIG. 6 is an enlarged cross-sectional detail view of the front portion of a plunger as shown in FIG. 3, with the elastomeric seal disposed in the position shown in FIG. 3.

Referring to FIGS. 2-3 and 6, annular recess 46 is deep enough to receive cooperatively sized and shaped annular positioning ring 44 when plunger seal 14 is mounted on tubular body 38 of plunger assembly 12, and has an inclined front wall and a square back wall. When elastomeric plunger seal 14 is mounted on the front end of tubular body 38, the open rear end is pressed over front tip 94 and annular positioning ring 44 so that the inwardly facing portion of plunger seal 14 at the rear end of annular recess 46 slides upwardly over the inclined front face of annular positioning ring 44 and along the top of annular positioning ring 44 until the forwardly facing square shoulder at the rear of annular recess 46 drops over the rearwardly facing square shoulder of annular positioning ring 44. As the body portion of plunger seal 14 reaches the position shown in FIGS. 3 and 6, the transverse web portion 58 of plunger seal 14 blocks and seals the opening in the front end of tubular body 38 that is defined by the blunt annular surface of front tip 94. As used herein, the term "blunt surface" is intended to differentiate a surface having edges that do not cut from a surface having edges that can cut, and it should be appreciated by those of skill in the art upon reading this disclosure that an injection molded plunger body or handle will have a front tip with a small radius on each edge that will prevent the plunger tip from cutting the transverse elastomeric web, particularly when the shear force exerted on the web by the tip is spread evenly around the circumference of the web as the web is stretched and thinned by rearward movement of the tubular body on the plunger.

Referring to FIG. 2, front tip 94 of tubular body 38 can define a single plane that is perpendicular to longitudinal axis 55 through syringe 10 or can be otherwise configured so that at least a portion of front tip 94 advances ahead of the remainder of front tip 94 as plunger 12 is advanced into barrel 24 to facilitate retraction as has previously been disclosed, for example, in U.S. Pat. No. 6,572,584. It will be appreciated whenever plunger 12 is advanced inside barrel 24 to facilitate retraction that front tip 94 of plunger 12 is desirably covered by plunger seal 14, thereby causing front tip 94 to contact retainer member 16 indirectly through plunger seal 14, or directly if transverse web portion 58 ruptures first.

Figure 7:
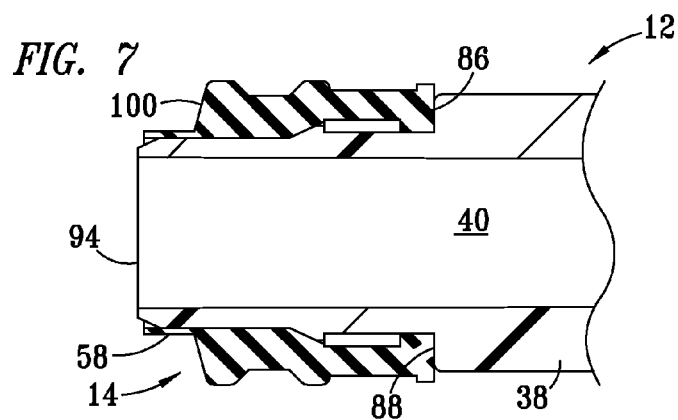
FIG. 7 is an enlarged cross-sectional detail view of the front portion of a plunger as shown in FIG. 5, with the elastomeric plunger seal displaced rearwardly from the position shown in FIGS. 3 and 6, with the portion of the plunger seal that previously extended across the end of the plunger having ruptured and contracted to the sides of the forwardly extending end of the plunger.
Figure 8:
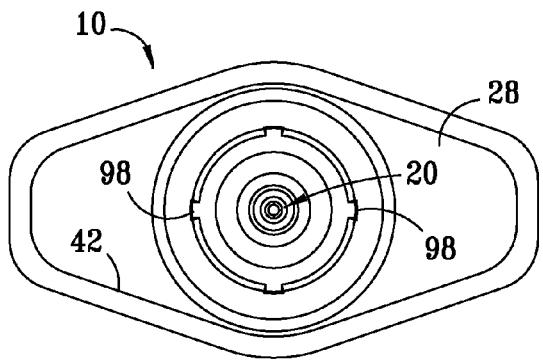
FIG. 8 is a bottom plan view of the medical device of FIG. 1.
Figure 9:
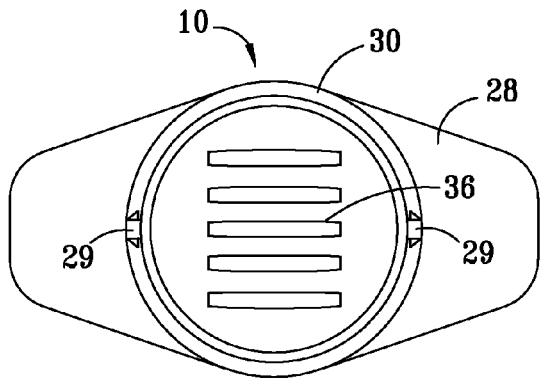
FIG. 9 is a top plan view of the medical device of FIG. 1.

Annular recess 46 of the annular body can have an axial length sufficient to permit plunger seal 14 to slide rearwardly on the outside of tubular body 38 and provide a predetermined range of travel between the position as shown in FIGS. 3 and 6, and the position as shown in FIGS. 5 and 7. When the body portion of plunger seal 14 is in its rearmost position relative to tubular body 38, annular surface 86 at the rear of plunger seal 14 can abut against forwardly facing annular shoulder 88 of tubular body 38 and the inclined front wall of annular recess 46 can likewise abut against the inclined front surface of annular positioning ring 44.

Referring to FIGS. 2 and 3, the needle retraction assembly can be assembled by applying retainer member 16 to larger-diameter section 62 of needle holder 18, inserting forward tip 70 and elongated tubular body portion 74 through compression spring 22, and then inserting retainer member 16, needle holder 18 and spring 22 into the rear of barrel 24 and advancing them forwardly inside barrel 24 until forward tip 70 extends through narrow opening 63 in the front of barrel 24 and forwardly facing annular shoulder 68 of needle holder 18 is blocked by a cooperating rearwardly facing annular shoulder 65 inside the front end of nose 76 of barrel 24. At the same time, spring 22 is compressed between the underside of larger-diameter section 62 of needle holder 18 and annular shoulder 65 inside nose 76. When the needle retraction assembly is in the position shown in FIG. 3, inside surface 80 of retainer member 16 provides a liquid seal between retainer member 16 and the outwardly facing surface of larger-diameter section 62 of needle holder 18, and outside surface 82 of retainer member 16 provides a liquid seal against the inside of tubular body 26 of barrel 24. The blunt, rearwardly facing end of needle 20 can then be inserted into the forwardly extending tip 70 of needle holder 18 and glued into place or otherwise attached by similarly effective known methods, thereby protecting the tip from insertion through the rear of barrel 24. When syringe 10 is assembled in this manner, fluid communication is established from the beveled, forwardly extending tip of needle 20, through axially extending chamber 84 and transversely extending pathways 69 of needle holder 18, and into fluid chamber 90 of barrel 24.

As plunger assembly 12 is advanced into barrel 24 during an injection, typically by pressing a thumb against thumb cap 36 of end cap 34 while simultaneously exerting rearward pressure against ridges 42 disposed around the front-facing surfaces of opposed flanges 28, plunger assembly 12 reaches a point where transverse web 58 contacts and flexes around the rounded, rearwardly projecting tip 64 of needle holder 18 as seen in FIG. 4. This causes fluid remaining inside chamber 90 of syringe 10 to be forced into fluid pathways 69 as annular front surface 100 of the body portion of elastomeric plunger seal 14 continues downwardly to a point where annular surface 100 is seated against inclined surface 102. As this happens, the pressure exerted rearwardly by inclined surface 102 against annular surface 100 causes the annular body portion of elastomeric seal 14 to move, slide, displace or stretch rearwardly relative to annular positioning ring 44 of tubular body 38. As the annular body portion of elastomeric seal 14 moves rearwardly relative to tubular body 38 of plunger 12, transverse web portion 58, preferably being integrally formed with the annular body portion, is stretched tautly over front tip 94 and is then distended rearwardly by rearwardly projecting tip 64 of needle holder 18. In this embodiment of the invention, neither front tip 94 nor rearwardly projecting tip 64 of the needle holder 18 is sharp enough to function as a cutter prior to the time that projecting tip 64 pierces or punctures stretched transverse web 58.

The continued application of thumb force to thumb cap 36 of plunger assembly 12, which in practice occurs as one smooth, continuous motion, causes rearwardly projecting tip 64 of needle holder 18 to rupture transverse web 58 and allows front tip 94 of plunger body 38 to contact, either directly or indirectly (if transverse web portion 58 ruptures before contact is made), and push retainer member 16 forwardly off of large-diameter section 62 of needle holder 18, thereby allowing compressed spring 22 to push needle holder 18 and at least part of needle 20 rearwardly into retraction cavity 40 inside plunger body 38, with the beveled front tip of needle 20 also being drawn inside and confined within barrel 24. Referring to FIGS. 4, 5 and 7, because the ruptured transverse web portion 58 is desirably elastomeric and because it was tightly stretched across the opening defined by front tip 94 of plunger body 38 prior to rupturing, remnants of the transverse web can contract out of the path of front tip 94 as it contacts retainer member 16, and also out of the path of needle holder 18 and needle 20 as they are projected rearwardly by spring 22 to avoid hang-up during retraction. As a result, referring to FIGS. 5 and 7, needle 20 is retracted into barrel 24, the bottom of relaxed spring 22 remains seated on annular shoulder 65 inside nose 76, and annular rear surface 86 of the annular body portion of elastomeric plunger seal 14 moves toward annular shoulder 88 of tubular body 38 of plunger assembly 12. After retraction, the forwardly extending end of spring 22 does not necessarily have to remain seated on annular shoulder 65 inside nose 76.

FIGS. 10-12 depict another embodiment of the invention in which syringe 110 is made similarly to but slightly different than syringe 10 as discussed above. One readily noticeable difference in syringe 110 is the vent hole 116 that is provided through the wall of tubular body 114 of the plunger assembly to vent retraction cavity 150 as needle holder 118 and needle 122 are propelled rearwardly during retraction. Another readily noticeable difference in syringe 110 is the configuration of needle holder 118. Unlike needle holder 18, needle holder 118 has two opposed, relatively pointed cusps 140, 142 that cooperate to pierce the transverse web portion 148 of slidable elastomeric plunger seal 144. Because the cusps are opposed and do not extend circumferentially around the rearwardly extending head of needle holder 118, medicine can enter the centrally disposed bore 166 of needle holder 118 and no transverse liquid flow paths such as fluid pathways 69 of needle holder 118 are needed to reduce the amount of ullage or "dead space" that could otherwise be present. Except for these noted differences, the structure, assembly and operation of syringe 110 of the invention are substantially the same as disclosed in relation to syringe 10.

Referring to FIG. 10, syringe 110 comprises barrel 112 into which plunger 114 is inserted in sealing engagement, which sealing engagement is provided by a unitarily molded, rubbery plunger seal comprising an annular body 144 and a transverse elastomeric web 148. When annular body 144 contacts inclined shoulder 155 as plunger 114 is advanced inside barrel 112 prior to needle retraction, annular body 144 can move rearwardly along annular surface 146 of plunger 114, thereby stretching elastomeric web 148. Retraction cavity 150 disposed inside plunger 114 has an open front end that is sealed by elastomeric web 148 and a closed rear end that is blocked by end cap 162. As plunger 114 is fully depressed inside barrel 112 during and following an injection, end cap 162 is desirably lodged into annular recess 164 of the barrel collar, making end cap 162 less graspable for subsequent withdrawal of plunger 114 from barrel 112.

In the front portion of barrel 112, needle holder 118 is seated in a position where annular shoulder 156 engages the inside of barrel 112 as front tip 158 of needle holder 118 extends forwardly out an opening at the front end of barrel 112. Referring to FIGS. 10 and 11, needle 122 is attached to needle holder 118 inside the centrally disposed bore 166 of elongated front section 120. The forwardly extending end of retraction spring 124 is also seated against an annular shoulder at the front of barrel tip 112, and the rearwardly facing end of compressed spring 124 is contacting and exerting a biasing force against a forwardly facing annular shoulder 128 of a larger-diameter section 126 of needle holder 118. Needle holder 118 is held in place prior to retraction by compressed elastomeric retainer ring 130 that also provides a fluid-tight seal between needle holder 118 and the inside wall of barrel 112. Annular space 154 is desirably provided forwardly of retainer ring 130 to facilitate retraction as discussed below in relation to FIG. 12. Referring again to FIG. 10, a sealed liquid containment chamber 147 is thereby provided inside barrel 112 between retainer ring 130 and the annular body 144 and elastomeric web 148 of the plunger seal, with the only remaining fluid pathway being through the bore of needle holder 118 and needle 122.

Referring to FIG. 10 and, by comparison, 12, as plunger 114 is advanced fully into barrel 112 by thumb pressure from the user following in injection, rearwardly projecting structures 140, 142, best seen in FIG. 11, contact and rearwardly distend or displace elastomeric web 148. As this occurs, the annular body of plunger 114 advances against the opposed annular shoulder 155 inside barrel 112, which causes annular body 144 to move rearwardly, stretching elastomeric web 148 more tautly as plunger 114 continues to move forward relative to barrel 112. When the front end of the plunger, acting through the plunger seal, contacts and pushes retainer ring 130 forwardly into space 154, projections 140, 142 rupture elastomeric web 148 and retainer ring 130 releases needle holder 118 to effect retraction of needle 122 into barrel 112 as needle holder 118 is pushed into retraction cavity 150. Following retraction, as seen in FIG. 12 in comparison to FIG. 11, annular body 144 of the plunger seal is displaced toward annular wall 145 of plunger 114. Retainer ring 130 remains in annular space 154, spring 124 is relaxed, and needle holder 118 and needle 122 are all disposed inside the retraction cavity of plunger 114. As depicted in FIG. 12, needle holder 118 and needle 122 are rotated 90 degrees from the position shown in FIGS. 10 and 11 to better illustrate flanges 164 and projection 140.

Another embodiment of the invention is described and explained in relation to syringe 200 as shown in FIGS. 13-17. FIG. 13 depicts syringe 200 as it might be packaged, shipped and stored. Syringe 200 preferably comprises barrel 202, plunger 204 inserted into and slidably engaging the inside wall of barrel 202, and protective cover 206 covering needle 236 as seen in FIG. 14. As previously noted in relation to syringe 10, needle cover 206 is shown in FIGS. 13-15 to illustrate how such a cover can be constructed and releasably attached to the front end of barrel 202 to protect needle 236 from being accidentally dulled or bent prior to use. Needle cover 206 is desirably releasably attached to the front of barrel 202 by frictional engagement, although it will be appreciated that such frictional engagement can be implemented in various ways known to those of skill in the art. For example, the frictional engagement can be achieved by using an annular snap ring, cooperatively tapered conical or ribbed surfaces, threads, or the like, that are disposed either inside the cap, or on the nose portion of barrel 202, or both. By providing a cap that has a wider opening at the end facing barrel 202, it is possible to use the cap as a guide during assembly. According to one preferred embodiment of the invention, the front tip of needle cover 206 is open to allow the cap to breathe and to permit mold core pins to be pulled from each end. When used with syringes 202 having detachable needles, the cap can even be used as a wrench to help secure a threaded needle tip to the front end of a needle holder, or to assemble a front-end attachment comprising a needle to the barrel.

Referring next to FIG. 14, plunger 204 of syringe 200 further comprises a molded end cap 210 having a removable insert 208; a plurality of circumferentially spaced, axially extending ribs 212 to provide rigidity to plunger 204 and to minimize possible frictional contact between plunger 204 and barrel 202; a plunger seal having an annular body portion 220 that can be seated around the tip of plunger 204 over annular boss 214 and can slide rearwardly across recess 218 toward shoulder 216 of plunger 204 to facilitate retraction. The plunger seal also has a transverse elastomeric web portion 242 (FIG. 15) that provides a seal over the forwardly facing open end of plunger 204 prior to retraction. Annular boss 214 on the outside of plunger 204 is received inside cooperating annular recess 240 of annular body 220 and provides sufficient holding force to prevent plunger 204 from pulling out of the plunger seal as plunger 204 is pulled rearwardly inside barrel 202 during aspiration.

The needle retraction assembly of syringe 200 as shown in FIG. 14 comprises a needle holder having two parts that are threaded together to facilitate changing needles if needed. Needle base 234 has a male threaded section that is releasably engageable with the female threaded front end portion 228 of elongated body section 226 below larger-diameter head section 224 that further comprises at least one rearwardly facing projection 246 as described in more detail in relation to FIG. 15. During assembly of syringe 200, elastomeric retainer ring 222 is stretched slightly so that it can be applied over head portion 224 of the needle holder. Front end portion 228 of the needle holder is inserted into spring 256, which is compressed around body section 226 and inserted into barrel 202 until both body section 226 and spring 256 are seated inside barrel 202 and retainer ring 222 is compressed sufficiently against the inside of barrel 202 to prevent spring 256 from expanding and to establish a liquid seal between head portion 224 of the needle holder and inside wall of barrel 202. In the embodiment shown (FIG. 15), a small annular bump 272 is also provided on the inside wall of barrel 202 to provide additional frictional support and engagement between retainer ring 222 and the inside wall of barrel 202. Following installation of the needle retraction assembly, the assembled plunger, with plunger seal 220 attached, can then be inserted into open collar at the rear of barrel 202 to slidably engage the inside wall.

Needle base 234, with or without needle 236 already attached, is then threaded into engagement with front end 228 of body section 226 of the needle holder seated inside barrel 202. Depending upon the internal configuration of needle cover 206, it can possibly be used as a wrench to turn needle base 234 to engage the threads with those of body section 226. At the same time, rearwardly facing open end 261 of needle cover 206 can be placed around the forwardly extending nose of barrel 202 to help align needle base 234 and threaded end 228 of body section 226 for achieving proper threaded engagement. If desired, it will be appreciated that needle base 234 can likewise be attached prior to inserting plunger 204 inside barrel 202.

FIGS. 15-16 further depict in more detail the internal structure of assembled syringe 200. Barrel 202 comprises opposed flanges 232 near the rear end that provide gripping surfaces for the user's fingers and prevent syringe 200 from rolling off a support surface. Rearwardly extending collar 230 is desirably provided behind flanges 232 and comprises recess 238 adjacent to the open rear end of barrel 202. Recess 238 is desirably sized and positioned so that the perimeter of plunger end cap 210 is disposed in close association with, and preferably nested inside, collar 230 following needle retraction. Insert 208 is provided with vent 209 for retraction cavity 244, and also facilitates the insertion and removal of a core pin during molding.

In the embodiment shown in FIG. 15, a small annular snap ring 258 comprising a cooperatively sized and aligned boss and recess disposed inside front section 260 of needle cover 206 near the front of needle base 234 is provided to provide frictional engagement between needle cover 206 and syringe 200. This allows the sidewall of cover 206 to be spaced slightly apart from nose 268 of barrel 202. Opening 262 is desirably provided at the front end of front section 260, but sterility is not adversely affected because syringe 200 is stored inside a sterile wrapper until the time of use, when cover 206 is removed in any case.

Needle 236 is desirably attached to needle base 234 by glue (or by another similarly effective attachment method) disposed inside annular recess 254, and needle base 234 is releasably attached to the inside of needle holder body 226 by cooperating threads 264, 266. Retraction spring 256 is compressed inside the annular space between nose 268 and needle holder body 226. Spring 256 is held in compression by retainer ring 222 disposed around needle holder head 224. Rearwardly facing, projection 246 at the rear of the needle holder is centrally disposed and comprises a plurality of circumferentially spaced inclined buttresses providing lateral support. Rounding the tip of projection 246 allows elastomeric web 242 to be distended rearwardly a greater distance than would otherwise be possible prior to rupturing during retraction. Transverse flow channel 248 desirably provides fluid communication with bore 250 of the needle holder to allow fluid to flow into or out of liquid containment chamber 270 of barrel 202 through needle 236. The projection 246, elastomeric web 242 and transverse flow channel 248 cooperate to provide greater utilization of the volume inside liquid containment chamber 270.

Figure 17:
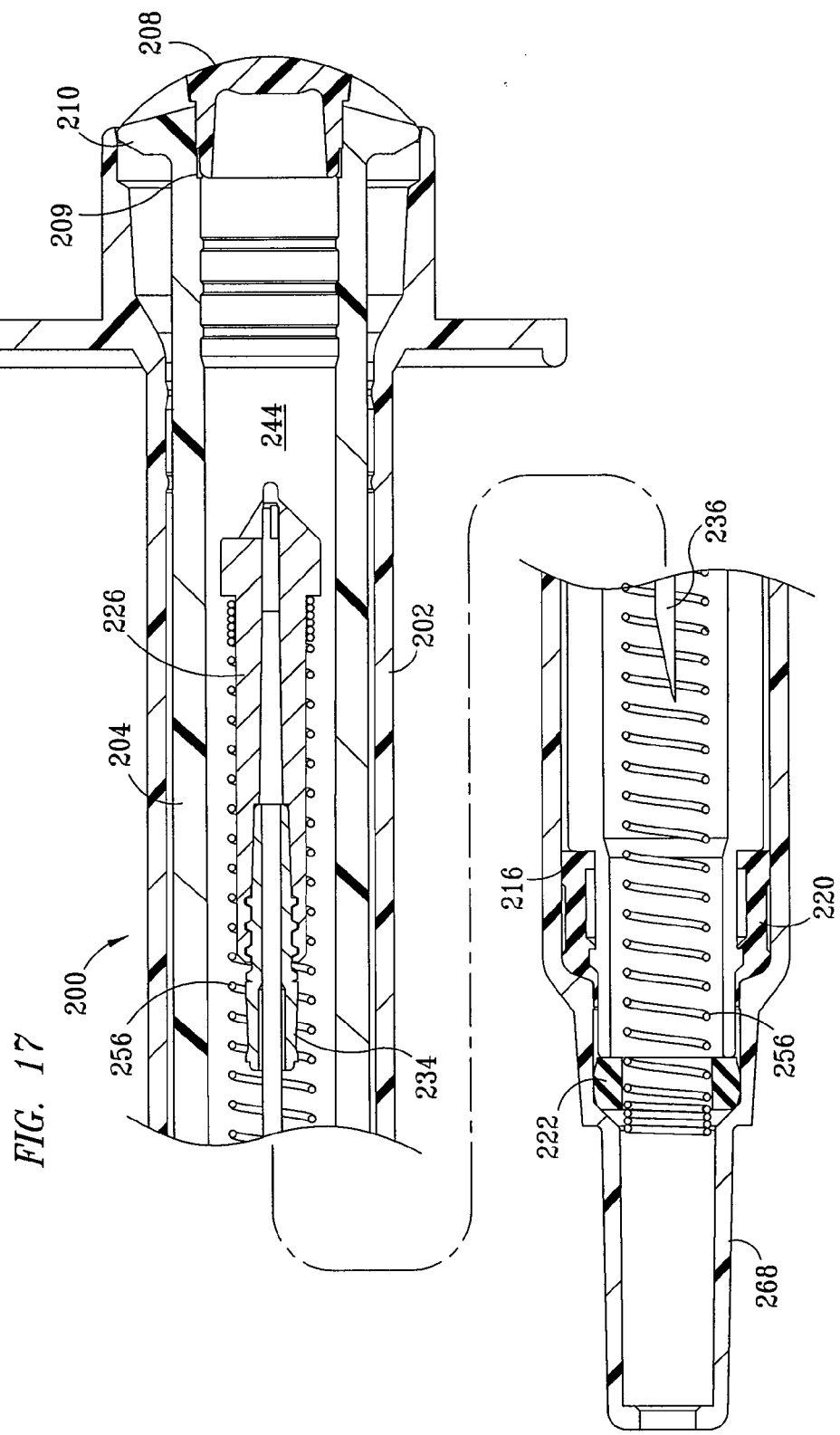
FIG. 17 is an enlarged, cross-sectional horizontal elevation view wherein the plunger is fully depressed inside the barrel and wherein the needle is fully retracted.

Referring now to FIG. 15 in relation to FIG. 17, as plunger 204 advances forwardly toward projection 246, the projection contacts elastomeric web 242, causing it to distend rearwardly into the retraction cavity, while the front portion of annular body 220 of the plunger seal contacts inclined annular shoulder 274 of barrel 202. As the plunger advance continues, annular body 220 slides rearwardly until it abuts against annular shoulder 216 of plunger 204, which also stretches and thins elastomeric web 242 to the point of rupture by projection 246. It should be appreciated upon reading this disclosure that the use of a rearwardly facing projection, even one that does not form a sharp point or edge, is likely to rupture the elastomeric web at the region of contact between the projection and the web prior to separation of the web from the annular body around the circumference of the plunger tip. This is believed to be because the stretching force exerted on the web by the annular body is spread evenly around the circumference, whereas the force exerted on the web by the projection is concentrated within a much smaller area.

As the plunger seal moves rearwardly on plunger 204, the front end of the plunger, acting through the plunger seal, contacts retainer ring 222 either directly or indirectly and begins to push it forwardly into annular space 252. Elastomeric web 242 desirably ruptures just before the needle holder is released by retainer ring 222. When the needle holder is released, spring 256 drives the needle holder rearwardly through the opening at the front of retraction cavity 244 of plunger 204 that is formed as the annular skirt that was previously elastomeric web 242 can snap back after elastomeric web 242 is ruptured by projection 246. Once elastomeric web 242 snaps back following penetration by projection 246, remnants of the web can in some cases remain disposed between the front tip of the plunger and retainer ring 222. In other cases, the front tip of the plunger can directly contact retainer ring 222 following needle retraction. In FIG. 17, needle holder body 226, needle base 234, needle 236 and all but the front end of spring 256 have been forced into retraction cavity 244 by the expanding spring. Although the length and diameter and post-retraction position of relaxed spring 256 can vary, needle 236 should remain inside barrel 202 following retraction for protection against accidental needle sticks.

Another embodiment of the medical device of the invention is disclosed in relation to FIGS. 18-23 of the drawings. Referring to these figures, medical device 300, which can be, for example, a hypodermic syringe, comprises barrel 302, a retractable needle assembly seated in the forward portion of barrel 302, and plunger 304 that is slidably inserted into an opening defined by substantially tubular collar 342 at the rear of barrel 302. Barrel 302 further comprises a pair of oppositely projecting, transverse flanges 326, 328 and a smaller-diameter nose section 336.

The retractable needle assembly is supported inside the front portion of barrel 302 and further comprises needle holder 308, elastomeric retainer member 310, compressed spring 312. Retainer member 310 provides a fluid seal between needle holder 308 and the inside wall of barrel 302. The forwardly extending end of compressed spring 312 is impeded from forward movement relative to barrel 302 by a rearwardly facing annular shoulder 331 of nose section 336 that also engages a forwardly facing annular shoulder disposed near the front of needle holder 308. Fluid flow path through needle holder 308 is 334 preferably disposed between the bore of needle 314 and transverse fluid flow path 332, which is disposed just forwardly of rear tip 348 of needle holder 308.

Plunger 304 preferably comprises a substantially tubular wall defining a retraction cavity 330, the tubular wall having at least two circumferentially spaced, axially extending ribs 305 projecting radially outward to help maintain proper alignment between plunger 304 and barrel 302, leaving a smaller diameter section 318 of ribs 305. A larger diameter section 340 is desirably disposed at the rear of plunger 304 that is receivable inside, or into close association with the inside of, rear collar 342 of medical device 300. The tubular wall of plunger 304 defines a longitudinally extending retraction cavity 330 that is closed at its rear end by end cap 338 and at its front end by generally transverse elastomeric web 317 of plunger seal 316. Plunger seal 316 is seated on small outside diameter section 318 of plunger 304. A radially extending annular projection 322 having a sloped front shoulder and a relatively square back shoulder, or another similarly effective structure, is preferably provided to prevent plunger seal 316 from sliding off the front of plunger 304 during when plunger 304 is pulled rearwardly inside barrel 302 as can occur, for example, during aspiration of medical device 300.

The forwardly extending end 320 of the tubular wall of plunger 304 can have one portion that extends more forwardly than the other, thereby causing at least a portion of elastomeric web 317 to be canted slightly out of the transverse plane that is perpendicular to the common longitudinal axis of medical device 300. This also causes the portion of the forwardly facing surface of elastomeric web 317 that covers the most forwardly extending portion of stepped front end 320 to contact retainer member 310 of the retractable needle assembly first, thereby initially concentrating the user's thumb force on one side of retainer member 310 to initiate movement of retainer member 310 relative to needle holder 308 and the inside wall of barrel 302.

Figure 18:
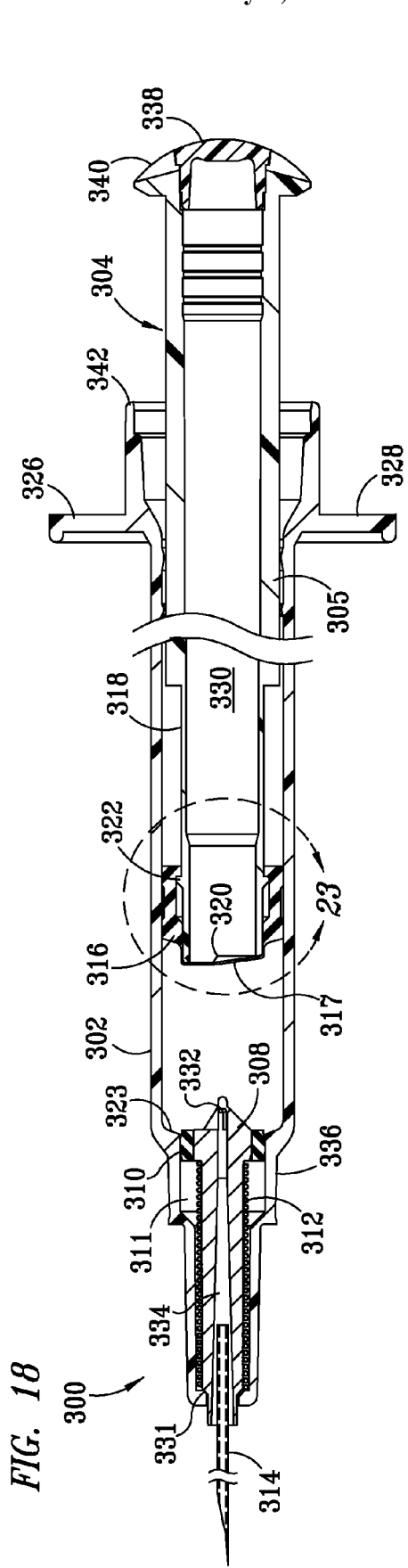
FIG. 18 is a cross-sectional elevation view of another embodiment of the medical device of the invention when disposed in a horizontal position, wherein the plunger handle has a stepped-front.
Figure 20:
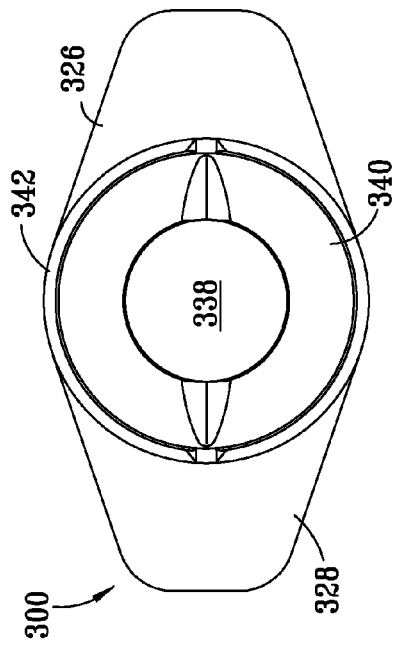
FIG. 20 is a right side elevation view of the entire (not in cross-section) medical device of FIG. 18.
Figure 19:
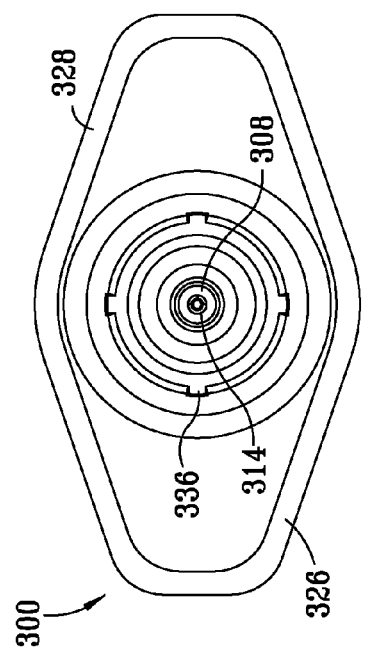
FIG. 19 is a left side elevation view of the entire (not in cross-section) medical device of FIG. 18.
Figure 23:
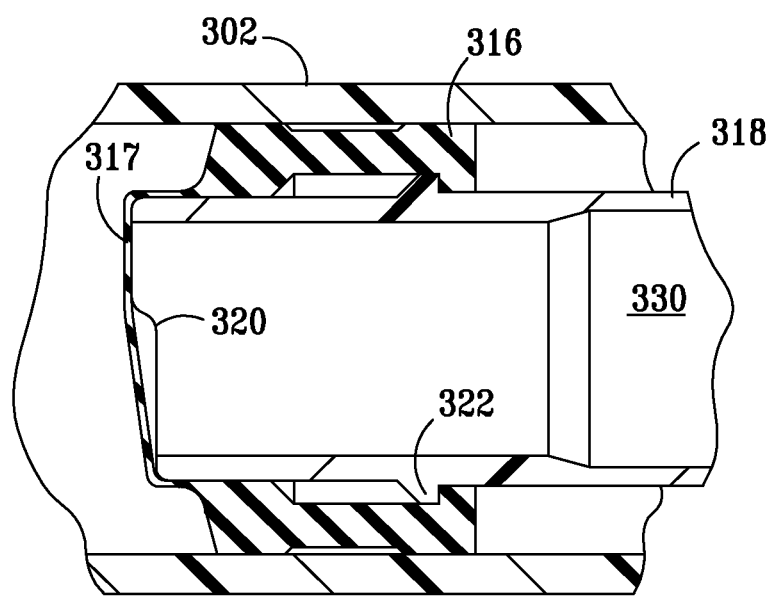
FIG. 23 is an enlarged detail view taken from FIG. 18 that better illustrates the stepped-front of the plunger portion of the subject medical device.

Referring to FIG. 18 in conjunction with FIG. 21, as plunger 304 is moved forwardly inside barrel 300, elastomeric web 317 eventually contacts projection 348 of needle holder 308, causing elastomeric web 317 to be stretched over the rearwardly extending portion of the needle holder and distended rearwardly a slight distance into retraction cavity 330. As plunger 304 continues to move forwardly, the forwardly facing annular shoulder of plunger seal 316 contacts the inwardly tapering shoulder 323 of barrel 302 adjacent nose 336, thereby causing plunger seal 316 to slide rearwardly on small diameter section 318 of plunger 304 to the position shown in FIG. 22. As this occurs, front end 320 of plunger 304 causes retainer 310 to be pushed forwardly into space 311 (FIG. 21) to the position shown FIG. 22. As this occurs, elastomeric web 317 ruptures, and needle holder 308 is no longer constrained against the force exerted rearwardly by compressed spring 312. As depicted in FIG. 22 with reference also to FIG. 21, as spring 312 expands, needle holder 308 and needle 314 are driven rearwardly into the retraction cavity inside plunger 304. When medical device 300 is in the fully retracted position as shown in FIG. 22, all portions of the retractable needle assembly are disposed inside of barrel 302.

The barrel of the medical device of the invention can be made of plastic, glass or any other material suitable for the intended use. As used herein, the term "plastic" refers primarily to moldable thermoplastic polymers such as, for example, polyethylene and polypropylene, that can also contain other ingredients such as curatives, filler, reinforcing agents, colorants, and/or plasticizers, etc., and that can be formed or molded under heat and pressure. Where the subject device is intended for use in applications where the barrel can be in prolonged direct contact with therapeutic liquids that can interact with plastic or that can be degraded by substituents that can otherwise enter the liquid from plastic, plastic should not be used. The tubular body or handle of the plunger of the invention is also preferably made of plastic, and will not typically come into contact with a therapeutic liquid prior to retraction.

In the past, the elastomeric materials used to make plunger seals have often included crosslinked thermosetting rubbery polymers that are easily deformable but that are approved for use with pharmaceutical grade fluids and are not readily susceptible to leaching or gas migration. It has now been appreciated that the plunger seal of the present invention can be made of an injection moldable elastomeric material approved for use with the therapeutic fluids of interest that, when molded into the annular body portion that, is sufficiently rigid to provide a reliable liquid seal between the plunger handle and the barrel and to resist disengagement of the plunger handle from the plunger seal when the plunger is withdrawn, for example, during aspiration. Also, because the plunger seal is ideally unitarily molded from a single elastomeric material, the material used should be of sufficient thickness and toughness that it can be stretched and thinned prior to retraction, but not prematurely, and will also tear readily when penetrated by a rearwardly facing projection on the needle retraction assembly to permit retraction. An elastomer suitable for such use can be Uniprene® rubber having a Shore A hardness of about 45. The material used to make the retainer ring is preferably a crosslinked thermosetting rubber polymer that is more easily deformable than plastic and that is approved for use with pharmaceutical grade fluids and are not readily susceptible to leaching or gas migration.

The needle holder portion of the needle retraction assembly can also be made of plastic or glass, and the use of plastic is preferred. The needle holder can be made, for example, from polycarbonate or acrylonitrile-butadiene-styrene ("ABS"). Such polymeric resins and adhesives suitable for securing a needle to the needle holder (or the needle tip in case of a device having an attachable, detachable and/or changeable needle are commercially available. Similarly, compression springs, typically made of metal, that can be used in devices having retractable needles, are also known to those skilled in the art and are commercially available.

As used herein, the term "fluid" refers primarily to liquids, but can also include suspensions of solids dispersed in liquids, and gases dissolved in or otherwise present together within liquids inside the fluid-containing portions of the devices of the invention. Conventional, commercially available lubricants suitable for use with plunger seals can be used to further improve sealing and lower the force that must be applied through the plunger to use the devices of the invention and to effect retraction.

One advantage of the present invention is that when the thinned and tautly stretched elastomeric web 148 is ruptured, the rubbery material snaps back with sufficient speed and force that the resultant opening is sufficiently large for needle holder 118 and the front end of spring 124 to pass through without hang-up that could otherwise impede complete retraction of needle 122 into body 112. Another advantage of the present invention is that the thumb force required to initiate retraction is substantially lower than has previously been achievable in conventional, commercially available syringes having retractable needles. This is at least partly because the present invention has no plug that must be dislodged to gain access to the plunger cavity, partly because there is no cutting or breaking of plastic parts that is required to initiate retraction, and partly because there is no need for a two-piece plunger that must be operated to initiate cutting or breaking. Based upon preliminary testing, it is believed that the mean thumb force required to retract the needle is reduced by more than thirty percent (30%) through use of the structures and materials disclosed herein. It is believed that the sliding and stretching of the elastomeric web of the plunger seal at the moment of penetration by the needle holder contributes to a reduction in the thumb force required to initiate retraction.

Another advantage of the present invention is that the use of a moveable plunger seal with an annular body unitarily formed together with a transverse elastomeric web permits the use of manufacturing tolerances that are greater and more forgiving than those previously required to produce medical devices with plungers having internal retraction cavities that are sealed by a removable plug prior to retraction. Also, with the devices of the present invention, premature blowout because of pressure exerted on the plug by a fluid contained in the device is not a constraint.

Another operational advantage of the present invention is the smooth forward movement of the plunger to initiate retraction. This smooth release is directly attributable to the combined use of a slidable, rupturable plunger seal and an elastomeric retainer ring that is pushed into the release position by the continuous forward motion of the plunger without the bumps or jolts resulting from breaking plastic parts, dislodging plunger plugs, or the audible "click"s previously experienced in the use of syringes having retractable needles.

Other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventors are legally entitled.

What is claimed is:

1. A syringe comprising a barrel, a rearwardly biased needle retraction assembly disposed forwardly in the barrel, and a plunger assembly slidably engaging the barrel to define a fluid chamber disposed between the needle retraction assembly and the plunger assembly;
   the plunger assembly further comprising a plunger having a tubular body with a front tip defining an opening into a retraction cavity disposed inside the tubular body, and an elastomeric plunger seal disposed over and around the front tip and the opening;
   the elastomeric plunger seal further comprising an annular body portion that provides a fluid seal against the barrel and a transverse web portion that covers the opening into the retraction cavity;
   the barrel and the plunger assembly being cooperatively configured so that the annular body portion of the elastomeric plunger seal is pushed rearwardly on the tubular body of the plunger as the plunger is moved forwardly relative to the barrel prior to initiating needle retraction, thereby displacing and repositioning the annular body portion relative to the tubular body, and stretching and thinning the transverse web portion so that the transverse web portion is more easily ruptured by a rearwardly extending portion of the needle retraction assembly and contracts following rupture to a position outside the opening that does not block the opening into the retraction cavity.

2. The syringe of claim 1 wherein the annular body portion of the elastomeric plunger seal comprises a plurality of longitudinally spaced apart, outwardly facing annular ridges that slidably engage the barrel.

3. The syringe of claim 1 wherein the annular body portion of the elastomeric plunger seal comprises an inwardly facing annular recess.

4. The syringe of claim 3 wherein the tubular body of the plunger comprises an outwardly facing positioning ring that is received within the inwardly facing annular recess of the annular body portion of the elastomeric plunger seal.

5. The syringe of claim 1 wherein the rearwardly biased needle retraction assembly comprises a spring.

6. The syringe of claim 1 wherein the rearwardly extending portion of the needle retraction assembly comprises at least one rearwardly projecting structure that is configured to rupture the transverse web portion.

7. The syringe of claim 6 wherein the at least one rearwardly projecting structure is positioned to contact the center of the transverse web portion.

8. The syringe of claim 6 wherein the needle retraction assembly comprises at least two spaced-apart rearwardly projecting structures.

9. The syringe of claim 1 wherein the barrel has a front portion comprising a nose and wherein the needle retraction assembly is at least partially seated inside the nose.

10. The syringe of claim 1 wherein the syringe is a single-use syringe.

11. The syringe of claim 1 wherein the front tip of the tubular body of the plunger comprises a stepped front end.

12. The syringe of claim 1 wherein the needle retraction assembly comprises a needle that is releasably attachable to the needle retraction assembly and can be changed prior to rupture of the transverse web portion.

13. The syringe of claim 1 wherein the front tip of the tubular body of the plunger is configured to concentrate a forwardly directed force applied through the plunger against a portion of the needle retraction assembly.

14. The syringe of claim 1 wherein the tubular body of the plunger further comprises a plurality of circumferentially spaced, axially extending ribs disposed a sufficient distance behind the elastomeric plunger seal to permit rearward movement of the elastomeric plunger seal prior to needle retraction.

* * * * *